United States Patent [19]
Li

[11] Patent Number: 6,114,154
[45] Date of Patent: Sep. 5, 2000

[54] METHOD OF CONSTRUCTING FULL-LENGTH TARGET CDNA MOLECULES

[76] Inventor: Huiwu Li, 5625 Midwood Ave., Apt. D, Baltimore, Md. 21212

[21] Appl. No.: 09/118,752

[22] Filed: Jul. 17, 1998

Related U.S. Application Data

[63] Continuation-in-part of application No. 08/937,365, Sep. 29, 1997, abandoned.

[51] Int. Cl.[7] .................................................. C12P 19/34
[52] U.S. Cl. ........................................................ 435/91.51
[58] Field of Search ........................................... 435/91.51

[56] References Cited

PUBLICATIONS

U. Gubler, et al., "A Simple and very efficient method for generating cDNA libraries", Gene, vol. 25, pp. 263–269 (1983).
G. Heidecker et al., "A Method for Cloning Full–Length cDNA in Plasmid Vectors", Methods in Enzymology, vol. 154, pp. 28–41 (1987).
C. Colecough, "Use of Primer—Restriction End Adapters in cDNA Cloning", Methods in Enzymology, vol. 154, pp. 64–83, 1987.
M. Frohman,, et al., "Rapid production of full–length cDNAs from rare transcripts: Amplification using a single gene–specific oligonucleotide primer", Proc. Natl. Acad. Sci., vol. 85, pp. 8998–9002, Dec. 1988.
C.M. Joyce, et al., "Construction of a plasmid that overproduces the large proteolytic fragment (Klenow fragment) of DNA polymerse I of Escherichia coli", Proc. Natl. Acad. Sci., vol. 80, pp. 1830–1834, Apr. 1983.
H. Aviv et al., "Purification of Biologically Active Globin Messenger RNA by Chromatography on Oligothymidylic acid–Cellulose", Proc. Nat. Acad. Sci., vol. 69, No. 6, pp. 1408–1412, Jun. 1972.
M.L. Kotewicz, et al. "Cloning and overexpression of Maloney murine leukemia virus reverse transcriptase in Escherichia coli", Gene, vol. 35, pp. 249–258 1985.
M. Kunitz, "A Spectrophotmetric Method for the Measurement of Ribonuclease Activity", J. Biol. Chem. vol. 164, pp. 563–568, 1946.
T. Arima et al., "Studies on Extracellular Ribonucleases of Ustilago sphaerogene, Characterization of Substrate Specificity with Special Reference to Purine–Specific Ribonucleases", Biochem. J. vol. 106, pp. 609–613, 1968.
R. Roychoudhury et al., "Terminal tranferase–Catalyzed Addition of Nucleotides to the 3'Termini of DNA", Methods in Enzymology, vol. 65, pp. 43–62, (1980).
H, Klenow, et al., "Selective Elimination of the Exonuclease Activity of the Deoxyribonucleic Acid Polymerase from Escherichia coli B by Limited Proteolysis", Proc. of the Natl Acad. of Sci., vol. 65, No. 2, pp. 168–175, Jan. 1970.
S.K. Batra, et al., "A Simple, Effective Method for the Construction of Subtracted cDNA Libraries", GATA, vol. 8, No. 4, pp. 129–133 (1991).
S. Henikoff, "Unidirectional digestion with exonuclease III creates targeted breakpoints for DNA sequencing", Gene, vol. 28, pp. 351–359 (1984).
I.R. Lehman et al., "The Deoxyribonucleases of Escherichia coli", Journ. of Bio. Chem., vol. 239, No. 8, Aug. 1964, pp. 2628–2636.
N.G. Nossal, "DNA Synthesis on a double–standed DNA template by the T4 Bacteriophage DNA Polymerase and the T4 Gene 32 DNA Unwinding Protein", Journ. of Bio. Chem., vol. 249, No. 17, pp. 5668–5676.
N.M. Calvin et al., "High–Efficiency Transformation of Bacterial Cells by Electroporation", Journ. of Bacter., vol. 170, No. 6, pp. 2796–2801, Jun. 1988.
W.J. Dower, et al., "High efficiency transformation of E. coli by high voltage electroporation", Nucleic Acids Research, vol. 16, No. 13, 1988, pp. 6127–6145.
P.T. Gilham, "The Synthesis of Polynucleotide–Celluloses and Their Use in the Fractionation of Polynucleotides", J. Am. Chem. Soc. vol. 86 p. 4982 (1964).
N. Harada, "A Unique Aromatase (P450aroM)mRNA Formed by Alternative use of Tissue–Specific Exons 1 in Human Skin Fibroblasts", Bio. and Biophy. Res. Comm., vol. 189, No. 2, pp. 1001–1007, 1992.
L. Chang, et al. "Enzymatic Synthesis of Oligodeoxynucleotides", Biochem. vol. 10, No. 3, pp. 536–542, 1971.

Primary Examiner—Terry McKelvey
Attorney, Agent, or Firm—Jones & Askew, LLP

[57] ABSTRACT

A method of direct construction and isolation of full-length target cDNA molecules obtains a large number of full-length target cDNA clones with minimum screening. This new method saves time and resources that are needed in traditional methods requiring large screenings of clones that do not contain the desired sequence. A characteristic of this method includes using a total RNA population to purify mRNA for synthesizing a mixed population of first strand cDNA. Another characteristic is the use of a short sequence of the target sequence as a forward primer for the generation of the second strand cDNAs and then separating out all non-hybridizing single stranded cDNAs. Only the double stranded cDNAs are then cloned and sequenced. In this manner, only target cDNA clones are obtained and a large amount of screening is avoided. Another characteristic is the use of directed expression of the cDNA during cloning by modifying each of the two ends of the cDNA with a different restriction enzyme, each end of the cDNA then being distinct and incompatible with the other end. The directional target cDNA is then ligated into a vector compatible with the ends of the directional cDNA. The vector-ligated cDNA is transformed into a bacterial host cell. The sequence of the isolated full-length target cDNA molecule is confirmed by sequencing.

17 Claims, 1 Drawing Sheet

Figure 1.

SEQUENCE LISTING

<160> NUMBER OF SEQ ID NOS: 4

<210> SEQ ID NO 1
<211> LENGTH: 39
<212> TYPE: DNA
<213> ORGANISM: murine
<220> FEATURE:
<221> NAME/KEY: primer_bind
<222> LOCATION: (1)..(20)
<223> OTHER INFORMATION: DNA primer
<220> FEATURE:
<223> OTHER INFORMATION: Description of Artificial Sequence: primer

<400> SEQUENCE: 1
atgttctgag cggccgccct ttttttttt ttttttttt                              39

```
<210> SEQ ID NO 2
<211> LENGTH: 37
<212> TYPE: DNA
<213> ORGANISM: murine
<220> FEATURE:
<223> OTHER INFORMATION: Description of Artificial Sequence: primer
<220> FEATURE:
<221> NAME/KEY: primer_bind
<222> LOCATION: (1)..(22)

<400> SEQUENCE: 2
agtatgcgaa cctgcaggga aggggggggg gggggggg                              37

<210> SEQ ID NO 3
<211> LENGTH: 20
<212> TYPE: DNA
<213> ORGANISM: murine
<220> FEATURE:
<223> OTHER INFORMATION: Description of Artificial Sequence: primer
<220> FEATURE:
<221> NAME/KEY: primer_bind
<222> LOCATION: (1)..(20)

<400> SEQUENCE: 3
taatacgact cactataggg                                                  20

<210> SEQ ID NO 4
<211> LENGTH: 19
<212> TYPE: DNA
<213> ORGANISM: murine
<220> FEATURE:
<223> OTHER INFORMATION: Description of Artificial Sequence: primer
<220> FEATURE:
<221> NAME/KEY: primer_bind
<222> LOCATION: (1)..(19)

<400> SEQUENCE: 4
gatttaggtg acactatag                                                   19
```

METHOD OF CONSTRUCTING FULL-LENGTH TARGET CDNA MOLECULES

This is a continuation-in-part of U.S. patent application Ser. No. 08/937,365, filed Sep. 25, 1997, now abandoned.

FIELD OF THE INVENTION

The present invention relates to the isolation of target cDNA molecules. More particularly, the invention relates to methods of direct construction of full-length target cDNA molecules with a primer from the target molecule, such that all isolated clones contain a full-length target cDNA.

BACKGROUND OF THE INVENTION

Several cDNA cloning strategies have been developed, however cDNA library cloning techniques rely on the selection and screening for expression of the gene of interest. Selection and screening can be time consuming and expensive. Also, traditional methods isolate partial target sequences, and the complete sequence must be pieced together from several clones or synthesized with techniques such as the Polymerase Chain Reaction.

Molecular cloning of cDNAs was first reported by Rougeon and Mach, *PNAS USA* 73, 3418–3422 (1976) and by Efstradiadis et al., *Cell* 7, 279–288 (1976). Since then, the technology has continued to be refined. Library cloning techniques are now commonplace and described in textbooks, such as, MOLECULAR CELL BIOLOGY, Darnell, Lodish and Baltimore (second edition, Scientific American Books, Inc., 1990). These techniques generally start with total RNA from cells. Generally, it is preferable to use mRNA from cells believed to synthesize the target protein. To make the complimentary DNA (cDNA), a short primer strand is hybridized to the mRNA near the 3' end. Most eukaryotic mRNA have a 3' poly(A)$^+$ tail, therefore, the primer is often poly(dT). Reverse transcriptase is then employed to add nucleotides to the primer to generate a cDNA, a DNA copy of the RNA molecule. The newly generated cDNA is called the first strand cDNA. The mRNA is then removed from the first strand cDNA, leaving the single stranded cDNA.

Next, a second strand cDNA is synthesized using the first strand cDNA as a template strand, to form a double stranded cDNA molecule. Double stranded cDNA can be made via several methods, for example, terminal transferase will add bases to a free 3' end of the single strand cDNA. If a poly(dC) tail is added to the 3' end of the first strand cDNA, then a poly(dG) primer and DNA polymerase can be employed to add nucleotides to the primer, thus creating the second strand cDNA. The second strand cDNA is annealed to the first strand cDNA and forms a complete double stranded DNA copy of the original mRNA.

The double stranded cDNA is then inserted into a plasmid vector having a marker. One method for inserting the cDNA into a plasmid vector involves cutting the plasmid vector with a restriction enzyme, and adding homopolymeric tails onto both ends of the cDNA and to both of the cut plasmid ends. Once the double stranded cDNA ends are annealed to the plasmid ends, the strands are joined by DNA ligase.

The plasmids are then transformed into an organism, such as *E. coli*, which lacks the marker of the plasmid vector. Cell colonies are grown and colonies having the marker are selected. For example, if the marker was ampicilin resistance and the cells were grown in the presence of ampicilin, only those cells having a plasmid conferring ampicilin resistance will grow. Then, radiolabeled DNA probe will be used to screen the cDNA library to look for the hybridized clones. Whether an inserted cDNA is present in the plasmid, and if so, if it is a partial or full-length target cDNA, is tested by sequencing and functional assays. It is common that many of the isolated and copied cDNAs, or clones, must be sequenced and analyzed before a partial or full-length target cDNA is isolated. This process of screening plasmids for a cDNA insert is expensive and time-consuming.

Okayama and Berg, *Mol. Cell. Biol.* 2, 161–170 (1982), transcribe mRNA into cDNA using a T-tailed cloning vector as primer. This method also requires a large amount of screening of plasmid vectors in search of vectors containing a partial or full-length target cDNA.

Gubler and Hoffman, *Gene* 25, 263–269 (1983), which describes synthesis of DNA in two steps by combining classical oligo(dT)-primed first-strand synthesis with RNase H-DNA polymerase I-mediated second strand synthesis. This method also requires a large amount of screening of plasmid vectors in search of vectors containing a partial or full-length target cDNA.

Heidecker and Messing, in *Meth. in Enz.* 154, 28–41 (1987), describe extending the 3' ends of a linearized pUC plasmid with thymidine residues. The oligo(dT) tails are annealed to the poly(A) tails of mRNA and are used to prime cDNA synthesis, thus covalently linking the cDNA to the vector DNA. The plasmid-cDNA molecules are extended with oligo(dG) tails, alkali denatured and sized on alkaline sucrose gradients (thereby also removing the RNA and denaturing the vector). An excess of oligo(dC)-tailed pUC plasmid is added. The vector strands are reannealed, the oligo(dC) tail of the second strand vector serves as primer for synthesis of the second strand of the cDNA insert after which the recombination plasmids are transfected into *E. coli*. This method also requires a large amount of screening of plasmid vectors in search of vectors containing a partial or full-length target cDNA.

In Coleclough, *Meth. In Enz.* 154, 64–83 (1987), single stranded cDNA is directly inserted into double stranded cloning vehicles with synthetic oligonucleotides called primer-restriction end adapters, which serve both as primers for polymerase reactions and as ligation substrates. This method also requires a large amount of screening of plasmid vectors in search of vectors containing a partial or full-length target cDNA.

Another method of obtaining full length cDNA clones is the "RACE" protocol, described in Frohman et al., *Proc. Natl. Acad. Sci. USA* 85, 8998–9002 (1988). The RACE method obtains cDNA clones from rare transcripts, that is, those having a low-abundance of mRNAs. An mRNA selection step is required. Then, cDNA clones are generated by using a modified version of the DNA polymerase chain reaction technique to amplify copies of the region between a single point in the transcript and the unknown 3' or 5' end. The method requires a single primer which must be a short stretch of sequence within the mRNA to be cloned.

In Joyce et al., *Proc. Natl. Acad. Sci. USA* 80, 1830–1834 (1983), mass production of the Klenow fragment by directed expression during cloning is described. However, this method also requires a large amount of screening for expression of the lacZ gene, screening by an alkaline lysis procedure, assays for β-galactosidase activity and characterization of fusion junctions by DNA sequence analysis.

SUMMARY OF THE INVENTION

The present invention comprises methods and compounds of direct construction and isolation of full-length target cDNA molecules. These novel methods and compounds can be used to obtain a large number of full-length target cDNA clones with minimum screening. These novel methods and compounds save time and resources that are needed by traditional methods requiring large screenings of isolated cloning vectors for those that contain the desired cDNA sequence.

Figure 1:
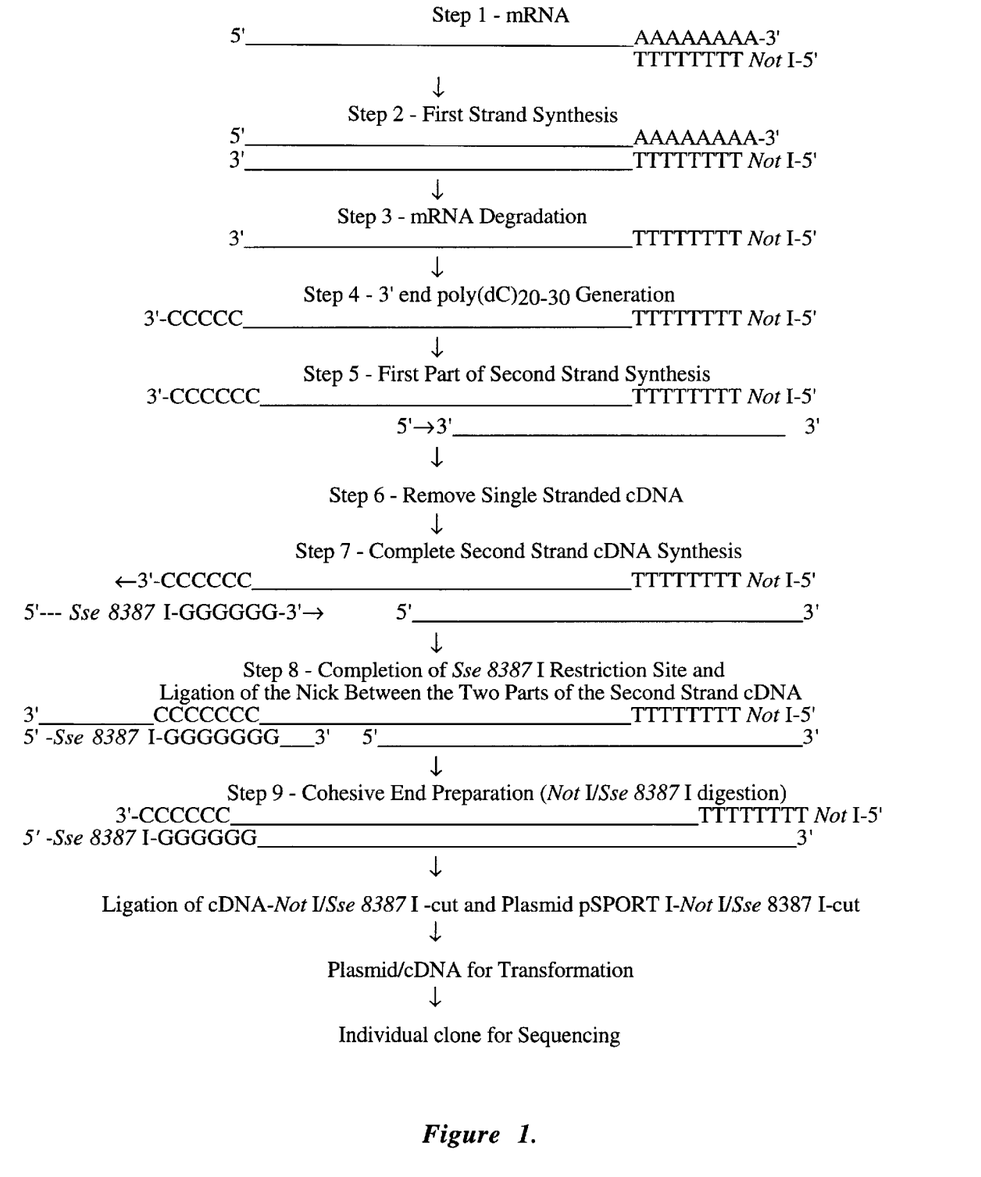
FIG. 1 is a flow chart showing an embodiment of the present invention.

A preferred embodiment of the methods of the present invention is summarized in FIG. 1. First, a mixed population of mRNA is obtained, using known techniques, from any biological source. First strand cDNA synthesis from the entire mRNA population is primed with a poly(dT)$_{20}$-Not I adapter. With this particular primer, a Not I site is strategically added to the 5' end of the first strand cDNA. The mRNA strands are degenerated. A poly(dC)$_{20\text{-}30}$ tail is polymerized on the 3' end of the first strand cDNA.

The primer for the synthesis of the second strand cDNA ensures isolation of only cDNAs of interest. A sequence fragment from the target DNA is used as the primer for the second strand synthesis. Only first strand cDNA sharing this sequence will hybridize with the primer and be duplicated in the 5' to 3' direction. These double stranded cDNAs are then separated from the single stranded cDNA. Because the primer may not have hybridized on the 3' end of the first strand cDNA and thereby they may not provide a full-length cDNA, the 3' end of the first strand cDNA must also be duplicated. This is accomplished by employing as a primer an Sse 8387 I adapter-poly(dG)$_{16}$-primer. The poly(dG) portion of this primer will hybridize to the poly(dC)$_{20\text{-}30}$ tail that was polymerized on the 3' end of the first strand cDNA and strategically adds an Sse 8387 I restriction site to the 5' end of the second strand cDNA. Then the space between the poly(dG)$_{16}$-primer and the previously duplicated section of the target cDNA is filled in.

Next, cohesive termini on both ends of the double stranded target cDNA and in a suitable vector are produced by digestion with restriction enzymes Not I and Sse 8387 I. The double stranded cDNA and the vector are then ligated together and the vector-ligated cDNA is transformed into a bacterial host cell. The host cells are grown and the target cDNAs isolated through standard techniques. The isolated full-length target cDNA molecule is confirmed by sequencing the double stranded cDNA fragment with T7 and SP6 primers.

A characteristic of the methods of the present invention comprises the use of an entire RNA genome to synthesize a mixed population of mRNA to synthesize a mixed population of cDNA for use in the production of the target cDNA.

Another characteristic of the methods of the present invention comprises using a short stretch of the DNA target sequence as a forward primer (as opposed to a poly(dG) primer) for the generation of the second strand cDNA and then separating out all non-hybridizing single stranded cDNA. Only the double stranded cDNAs are then synthesized to full-length, cloned and sequenced. In this manner, only target cDNA clones are obtained and a large amount of screening is avoided.

Another unique step in the preparation of full-length target cDNA of the methods of the present invention includes inserting the cDNA into the vector in a specific orientation for directed expression during cloning. Imparting a specific orientation is important for understanding that the outer strand cDNA in the vector represents the mRNA in the same direction and same sequence. Also, T7 may now be used as a promoter in functional studies, but not SP6. Finally, one can synthesize the antisense RNA with SP6 RNA polymerase.

Insertion of the cDNA in a specific orientation is accomplished by cutting the ends of the cDNA with two different restriction enzymes. By cutting one end with one enzyme and the other end with a different enzyme, each end of the cDNA is then distinct and incompatible with the other end. The directional target cDNA is then ligated into a vector compatible with the ends of the directional cDNA.

It is an object of the present invention to provide methods of obtaining full-length target cDNA clones without having to construct a cDNA library and to screen an excessive number of clones.

It is also an object of the present invention to provide methods to obtain a large number of copies of a full-length clone on the first screen.

It is an object of the present invention that only target cDNA is isolated, amplified and sequenced thereby saving time and expense in screening and sequencing many clones when isolating the full-length target.

It is an object of the present invention that no fragments of target molecules from cDNA libraries are competing with the full-length cDNAs for ligation into the vector.

It is an object of the present invention that the methods can be performed without the use of radioactive reagents.

It is an object of the present invention that double stranded target cDNA clones are separated from single stranded (non-target) cDNA clones with oligo (dA) cellulose.

DETAILED DESCRIPTION OF THE INVENTION

The methods, intermediate compounds and compounds used in the disclosed invention for isolating full-length cDNA clones of a target molecule from an mRNA population are described below. FIG. 1 and the following examples provide a detailed disclosure of one embodiment of the invention. It will be understood by those in the art that alternate techniques in many of the following steps may be employed. For example, alternate techniques may be used in the preparation of mRNA, in the separation of single stranded and double stranded cDNA, and in the introduction of vectors into the host cells. Other variables include substitution of the particular vectors and bacterial host cells employed in this disclosure as well as the restriction enzymes used for directed expression of the cDNA.

1. mRNA Isolation

The construction and isolation of full-length cDNA of a target molecule relies on the preparation of a high quality mixed population of template mRNA. Extraction of total RNA may be from different biological sources. A preferred extraction method is with Tri-zol Reagent [TRIzol®reagent, Cat.No.: 15596, Life Technologies]. Preferably the mixed population of template mRNA is purified over an affinity column [oligo (dT) cellulose, Bethesda Research Laboratories, Cat. No.: 15940–018] twice to select polyadenylated [poly(A)$^+$] RNA from total RNA (Aviv et al., *Proc. Nat. Acad. Sci.* USA 69:1408–1412 (1972)).

Generally, 5 μg mRNA will be sufficient for one reaction to construct the full-length cDNA of target molecule in an mRNA population.

2. First Strand Synthesis

A reverse transcriptase that no longer contains RNAse H activity is recommended for the mixed population of first strand cDNA synthesis from the mixed population of template mRNA. A preferred reverse transcriptase is Modified Moloney Murine Leukemia Virus (M-MLV RT).

A preferred primer is a poly(dT)-adapter having a recognition sequence for a rare enzyme, such as Not I or Sse 8387 I which occur approximately once in $10^6$ base pairs. The number of (dT)s in the primer is variable. In the disclosed embodiment the preferred hybridized primer is a poly(dT)$_{20}$-Not I adapter, 5'-pATGTTCTGA GCGGCCGCCC(T)$_{20}$-3' (SEQ ID NO:1) wherein the underlined portion is the Not I recognition site (Kotewicz et al., *Gene* 35:249–258 (1985); Coleclough, *Meth. Enz.*, 154, 64–83 (1987)). (See FIG. 1, Steps 1 and 2.) The poly(dT) portion of the primer anneals to the poly(A) tails of the template mRNA.

Preferred first strand synthesis reaction conditions are:

Reaction Temperature 37° C.

Reaction volume 20 μl

M-MLV RT 200 u/per μg mRNA

After completion of the mixed population of first strand cDNA sequences synthesis reaction (FIG. 1, step 2), the primary sequence of the hybridized template mRNA is degenerated by denaturation. This separates the mRNA from the first strand cDNA, and protects the cDNA from digestion of RNase A and RNase T$_1$ (Kunitz, *J Biol. Chem.* 164:563–568 (1946); Arima et al., *Biochem. J* 106:609–613 (1968)) (FIG. 1, step 3.)

3. Adding Deoxyribonucleotides(dC)$_{20-30}$ to the 3' Ends of the First Single Stranded cDNAs Terminal Deoxynucleotideyl Transferase generates poly (dC)$_{20-30}$ tails on the 3' ends of the first strand cDNAs (Roychoudhury, *Method in Enzymology* 65:43–62 (1980)), which are the most preferred substrate for the enzyme. (FIG. 1, step 4). The optimal reaction conditions of generating 20 to 30 residues include a temperature of 37° C., and a reaction time of approximately 10 min. The reaction is terminated by adding 20 μl of 0.5 M EDTA and subsequent phenol extraction.

4. Second Strand Synthesis of Target Molecule

To generate target cDNA a short stretch of the target DNA sequence is added to the first strand cDNA mixed population as a forward primer under conditions allowing for hybridization. Only target first strand cDNAs have the complementary target sequence, so only target first strand cDNAs will hybridize with the forward primer. Non-target first strand cDNAs remain single stranded.

The length of the forward primer is preferably between 10 to 50 base pairs, and more preferably between 22 and 35 base pairs. In FIG. 1, step 5, the primer is shown as "5'→3'". Preferably the primer hybridizes in the middle or close to the 3' end of the first strand cDNA sequences. Upon hybridization of the primer, only this hybridized first strand cDNA can be used as a template in second strand cDNA synthesis.

The synthesis of the second strand between the forward primer and the 3' end of the second strand cDNA sequences is catalyzed with a DNA dependent DNA polymerase, such as Klenow (Klenow et al., *Proc. Nat. Acad. Sci.* USA 65:168–175 (1970)). Double stranded target cDNA is now formed.

The optimal reaction conditions for the second strand cDNA synthesis are:

Reaction Temperature 37° C.

Reaction Volume 50 μl

Klenow Fragment 5–10 u

5. Purification of Double Strand cDNA

A distinguishing difference between the double stranded cDNA and the leftover single stranded cDNAs is that the single stranded cDNAs have exposed poly(dT)$_{20}$ tails on the 5' ends. FIG. 1, step 5 shows the double stranded target molecule, wherein the poly(dT)$_{20}$ tail has been covered by the newly synthesized second strand cDNA. Therefore an affinity column of oligo (dA) cellulose is a preferred method for separating and isolating the double stranded target cDNA from the non-target single stranded cDNAs (Batra et al., *GATA* 8:129–133 (1990)). Preferably the double stranded cDNA is run through the affinity column twice.

To ensure that no copies of the single stranded cDNA exist in the last elution of double stranded cDNA, residual single-stranded cDNA can be further degraded by the addition of a 5' exonuclease, such as mung bean nuclease [5'→3' exonuclease, United States Biochemical, E.C.3.1.30.1.] (Henikoff, *Gene* 28:351–359 (1984)).

6. Directional Cloning Construction—Completion of the Second Strand cDNA Synthesis and Introducing Asymmetry into cDNA Directional expression during cloning is obtained by introducing two different restriction endonuclease sites at the ends of the cDNA. The Not I site was previously added to the 5' end of the second strand cDNA in part 2 of the Detailed Description and shown in Steps 1 and 2 of FIG. 1. Now an Sse 8387 I site will be hybridized to the 3' end of the first strand cDNA, to be incorporated into the 5' end of the second strand cDNA.

First a poly(dG)-primer-Sse 8387 I adapter, 5'-pAGTATGCGAACCTGCAGGGAA(G)$_{16}$-3' (SEQ ID NO:2) wherein the underlined portion is the Sse 8387 I recognition site, is hybridized to the poly(dC)$_{20-30}$ tail on the 3' end of the first strand cDNA sequences. The number of (dG)s in the primer is variable. In the disclosed embodiment, the poly(dG)$_{16}$primer-Sse 8387 I adapter will prime the completion of the second strand cDNA synthesis between the 5'-Sse 8387 I adapter-poly(dG)-primer-3' and the forward primer after the unpaired deoxynucleotide on 3' ends of both Sse 8387 I adapter-poly(dG)$_{16}$-primer and first single strand cDNA with Exonuclease I (United States Biochemical, Cat. No.: 70073) are removed (Lehman et al., *The J Biol Chem.* 239:2628–2636 (1964)). This creates a Sse 8387 I restriction enzyme site beyond the cap sequence of the double stranded cDNA shown in step 8 of FIG. 1. T$_4$ bacteriophage DNA polymerase is recommended for completing the second strand synthesis (Nossal, *J Biol. Chem.* 249:5668 (1974)), since it does not contain 5'→3' exonuclease activity during the elongation of the second strand and the first strand cDNA. Thus the double stranded target cDNA is modified into directional target cDNA, each double stranded target cDNA having two ends, one end of each of the double stranded target cDNA being distinct and incompatible with the other end, and a full-length double stranded target cDNA is formed.

The optimal reaction conditions are:

Reaction temperature 37° C.

Reaction volume 50 μl

Enzyme 20 u

A nick is left unfilled when the second strand cDNA sequences between the 5'-Sse 8387 I adapter-poly(dG)-primer-3' and the forward primer are synthesized. T$_4$ DNA ligase is preferred for sealing the nick in the double stranded cDNA. The optimal reaction conditions are:

Reaction temperature 22° C.

Reaction volume 50 μl

Enzyme 6 u

Before ligating the full-length double stranded target cDNA into a vector, restriction enzymes Not I and Sse 8387

I (United States Biochemical) are used to digest the nucleic acids on both the double stranded cDNA and the vector to create two different coherence terminus on the ends of cDNA and vector. A preferred vector is pSPORT 1 (Life Technologies, Cat. No.: 15382–013). The eight base recognition sequence of Not I and Sse 8387 I are chosen for their extreme rarity in most cDNAs, occurring approximately once in $10^6$ base pairs. This creates a directional target cDNA and a vector having compatible ends to the directional target cDNA.

7. Ligation of Double Stranded Target cDNA to the Plasmid Vector and Introduction into *E. coli*

The directional target cDNa is ligated into a vector compatible with the ends of the directional target cDNA. The ligation reaction (in Example 8) in the methods of the present invention will suffice for all applications. It is preferred that 10 ng of cDNA to 50 ng of cDNA vector is used in the ligation reaction (as little as 1 ng of cDNA can be used in the ligation reaction).

pSPORT 1 is chosen for its multifunctional capabilities. It acts as an expression vector for cDNA cloning, in vitro transcription, dideoxy DNA sequencing and is useful in subtraction library procedures. The plasmid contains a unique multiple cloning site with sites for 19 restriction endonucleases, including Not I and Sse 8387 I, flanked by SP6 and T7 RNA polymerase promoters. These promoters may be used to generate RNA for probes, in vitro translations, or subtracted cDNA libraries. DNA inserts can be sequenced from double strand DNA using SP6/T7 Forward or Reverse Sequencing Primers. The ampicilin-resistance gene on the plasmid provides for convenient selection. Any plasmid sharing these characteristics may be used in the embodiment shown in FIG. 1.

The ligated cDNA vector can be introduced into bacterial host cells, such as *E. coli*. A preferred means of introduction is electroporation (Calvin, *J. Bacteriol.* 170:2796–2801 (1988); Dower, *Nucl. Acids Research* 16:6127–6145 (1988)), which generally will yield a greater number of transformants (up to $1 \times 10^9$ transformants/$\mu$g of cDNA). However, any means of introduction of the ligated cDNA vector into the host cells will suffice.

8. Sequencing Confirmation of Isolated Full-length Target cDNA Insert

A. Titer Determination of the Transformants

Portions of the cells are plated on LB plates containing 100 $\mu$g/ml ampicilin. The equivalent of 1.0, 0.1, and 0.01 $\mu$l, are plated in serial dilution in LB medium. The plates are incubated overnight at 37° C. and the remaining transformed cells are stored at 4° C. overnight. The colonies on each plate are counted, the correct titer is determined, and are then plated at a density suitable for single colony isolation.

B. Sequence Confirmation of Target cDNA Molecule

Molecular biology techniques for confirming sequence are applicable for this invention. A preferred method for confirming the correct construct of target cDNA molecule is by plasmid purification with Wizard Lambda Preps DNA Purification System [Promega, Cat.No.: A7290] and double stranded DNA sequencing [Perkin-Elmer Applied Biosystems 377 Prism DNA Sequencer] with primers T7 and SP6 on both ends of the insert.

The invention also contemplates a kit for direct construction and isolation of full-length target cDNA molecules from a mixed population of mRNAs comprising adapter-primers, enzymes, buffering agents and oligonucleotides well known in the art for synthesizing cDNA and other reagents necessary for carrying out the other reactions described in this application. Also possible to be included is a plasmid vector, DEPC water and oligo(dA) cellulose.

EXAMPLES

Example 1

Total RNA Isolation

Combine 50–100 mg tissue or cells with 1 ml Tri-zol Reagent [Life Technologies]. Homogenize 40×1000 rpm, 1 min., twice. Keep for 5 min. at room temperature.

Phase Separation:

Add chloroform 0.2 ml/1 ml Tri-zol Reagent. Shake for 15 sec., 2–3 min at room temperature. Centrifuge sample at 12,000×g for 30 min in 4° C. Collect supernatant. Add isopropyl alcohol 0.5 ml/1 ml Tri-zol Reagent. Keep 10 min. at room temperature. Centrifuge 12000×g for 10 min in 4° C. Wash the RNA pellet with 75% ethanol 20 ml (−20° C.). Centrifuge at 7500×g for 5 min at 4° C., twice. Dry the sample 2–5 min. Redissolve the sample in DEPC treated water (total RNA).

Example 2 mRNA Purification

The construction and isolation of full-length cDNA of a target molecule relies on the preparation of high quality mRNA.

Total RNA preparation 4 mg Total RNA in DEPC Treated water 65° C., 10 min, ice, 10 min. Add concentrated NaCl to a final concentration of 0.5 M. (Total volume is 1 ml).

Affinity Column Preparation of Oligo (dT) Cellulose

Dissolve 0.25–0.5 g dry weight oligo (dT) cellulose in 1 ml elution buffer. Put on column and wash column with 30 ml elution buffer. Equilibrate the column with 30 ml of binding buffer.

Apply sample on the column and collect the elution, re-apply the sample at least two more times. Wash the column with 10 ml binding buffer. Elute the mRNA with 1 ml elution buffer. The collected elution is the mRNA.

Repeat the elution three more times with either a new column or a reactivated column. The eluted mRNA is immediately precipitated by 1/10(v/v) 3 M $CH_3COOK$ and two volumes of ethanol (−20° C.). Dry the pellet. Dissolve the mRNA with DEPC treated water to a final concentration of 2–3 $\mu$g/$\mu$l, store the sample in −80° C. for the next step.

| Binding buffer | Elution buffer |
| --- | --- |
| 0.5M NaCl | 10 mM Tris-HCl (pH 7.5) |
| 10 mM Tris-HCl (pH 7.5) | 1.0 mM EDTA |
| 1.0 mM EDTA | 0.2% SDS |
| 0.2% SDS | |

Example 3

First Strand cDNA Synthesis

Place poly(A)$^+$ mRNA (5.0 $\mu$g) in DEPC-treated water with 50 mg/ml Not I adapter-poly(dT)$_{20}$-primer.

Incubate at 70° C., 10 min. Keep on ice, 10 min.

| 10X Reaction buffer I |
| --- |
| 50 mM Tris-HCl (pH 8.3) |
| 75 mM KCl |
| 6 mM $MgCl_2$ |
| 10 mM DTT |
| 500 $\mu$M each dATP, dCTP, dGTP, dTTP |

Incubate at 37° C., 2 min. Add SuperScript II RT 30,000 u/ml and incubate at 37° C., 1 h. This completes the first strand synthesis (final volume 20 μl).

| Example of a 20 μl reaction: |
| --- |
| 2 μl mRNA |
| 13 μl water |
| 2 μl 10X Reaction Buffer I |
| 2 μl dNTP |
| 1 μl enzyme |

Precipitate

Add 130 μl DEPC-treated water, 70 μl of 7.5 M NH$_4$OAc (−20° C.), and 0.5 ml of absolute ethanol (−20° C.). Centrifuge for 10 min at 14,000×g, and remove the supernatant. Wash the pellet with 800 μl of 70% ethanol (−20° C.) and centrifuge. Dry the sample. The pellet will contain mRNA and the first strand cDNA.

mRNA Degradation

Add DEPC-treated water to the dried pellet and incubate at 100° C., 5 min. Keep on ice for 5 min. Add 10× RNase A, RNaseT1 reaction buffer and incubate at 37° C., 1 h (final volume 150 μl).

| RNase A, RNase T$_1$ reaction buffer |
| --- |
| 10 μM Tris-HCl (pH 7.5) |
| 0.4 μM EDTA |
| 100 μg/ml RNase A |
| 100 μg/ml RNase T$_1$ |

Extract, Precipitate

Add 150 μl of phenol:chloroform:isoamyl alcohol (25:24:1) and vortex thoroughly. Centrifuge at room temperature for 5 min at 14,000×g to separate the phase. Remove 145 μl of the upper aqueous layer to a fresh 1.5 ml microcentrifuge tube. Add 70 μl of 7.5 M NH$_4$OAc and 0.5 ml of absolute ethanol (−20° C.). Centrifuge for 20 min at 14,000×g. Remove the supernatant. Wash the pellet with 800 μl of 70% ethanol (−20° C.) and centrifuge. Dry the sample which now contains only single strand cDNA.

Example 4

Poly (dC)$_{20-30}$ Tail Generation on the 3' End of First Strand cDNA

Combine 1–10 μg of first strand cDNA (1–10 μg) with reaction buffer II to a final volume of 150 μl. Incubate at 37° C., 10 min.

| Reaction buffer II | |
| --- | --- |
| 100 μM | dCTP |
| 1 mM | MgCl$_2$ |
| 100 mM | Potassium cacodylate pH 7.0 |
| 200 μM | Mercaptoethanol |
| 60 u/pmole of 3'-OH end | Terminal Deoxynucleotidyl Transferase |

To terminate the reaction add 20 μl 0.5 M EDTA and 100 μl neutralized phenol:chloroform:isoamyl alcohol (25:24:1). Vortex thoroughly. Keep in 0° C., 10 min. Centrifuge at 14,000×g for 5 min. Collect the supernatant. Add 70 μl of 7.5 M NH$_4$OAc and 0.5 ml of absolute ethanol (−20° C.). Centrifuge for 20 min at 14,000×g, and remove the supernatant. Wash the pellet with 800 μl of 70% ethanol (−20° C.) and centrifuge. Dry the sample, which now contains only single strand cDNA with poly(dC)$_{20-30}$ tail.

Example 5

Priming and Beginning Second cDNA Strand Synthesis

The primer is a DNA fragment obtainable from many sources, such as GenBank, off the internet or a cDNA fragment. Preferably, the primer is a maximum of 50 base pairs. More preferably, the primer is between 22 to 35 base pairs.

Place the first strand cDNA in DEPC-treated water with 22 to 35 base pair primer (2 pmol/per reaction). Incubate at 100° C., 5 min. Place on ice for 5 min. Incubate at 65° C., 1 h. Place on ice, 10 min. Add reaction buffer III to a final volume of 50 μl and incubate at 37° C. for 1 hour.

| Reaction buffer III |
| --- |
| 67 mM KPO$_4$, pH 7.4 |
| 6 mM MgCl$_2$ |
| 1 mM 2-Mercaptoethanol |
| 35 μM each dATP, dCTP, dGTP, dTTP |
| Klenow Fragment of Polymerase I 5–10 u |

Extract Precipitate

Add 50 μl of phenol:chloroform:isoamyl ethanol (25:24:1). Vortex thoroughly. Centrifuge at 14,000×g for 5 min. Transfer the upper layer to a fresh 1.5 ml microcentrifuge tube. Add 12.5 μl of 7.5 M NH$_4$OAc and 150 μl of absolute ethanol (−20° C.). Centrifuge at 14,000×g for 20 min. Remove the supernatant. Wash the pellet with 800 μl of 70% ethanol (−20° C.) and centrifuge. Dry the sample, which now contains the partially complete double stranded cDNA and the non-hybridized single stranded cDNAs.

Example 6

Double Strand cDNA Purification from the First Strand cDNA Pool

Column Purification

Sample Preparation

Combine cDNA sample and DEPC-treated water. Add concentrated NaCl to a final concentration of 1.0 M. Adjust the final volume with DEPC-treated water to 100 μl.

Column Preparation

Mix 0.25 g dry weight oligo(dA) cellulose and 1 ml column preparation buffer. Put on column and wash with 30 ml column preparation buffer. Equilibrate the column with 30 ml binding buffer.

| Binding buffer | Column preparation buffer |
| --- | --- |
| 1.0M NaCl | 10 mM Tris-HCl pH 7.5 |
| 10 mM Tris-HCl pH 7.5 | 1.0 mM EDTA |
| 1.0 mM EDTA | |

Apply the sample on the column and collect the elution, apply the sample to the column at least two more times. Collect the last elution. Add 100 μl more binding buffer on the column and collect it. Repeat this procedure [oligo (dA) cellulose chromatography] before proceeding to the next step. The eluted double stranded cDNAs are immediately precipitated by adding 1/10 volume of 3 M CH$_3$COOK and two volumes of ethanol (−20° C.). Centrifuge at 14,000×g, 20 min, washing twice with 800 μl of 70% ethanol (−20° C.). Dry the pellet. Dissolve the double stranded cDNA in 5 μl DEPC-treated water.

Mung Bean Nuclease Digestion

Add 45 µl Reaction Buffer IV to the 5 µl of resuspended double-stranded cDNA. Incubate at 37° C. for 30 min (final volume 50 µl).

| Reaction buffer IV |
| --- |
| 30 mM NaOAc (pH 4.6) |
| 50 mM NaCl |
| 1 mM ZnCl$_2$ |
| 5% Glycerol |

Extract, Precipitate

Add 50 µl of phenol:chloroform:isoamyl ethanol (25:24:1) and vortex thoroughly. Centrifuge at 14,000×g for 5 min. Transfer the upper layer to a fresh 1.5 ml microcentrifuge tube. Add 12.5 µl of 7.5 M NH$_4$OAc, 5 µl yeast tRNA (GIBCO BRL, Life Technologies), and 150 µl of absolute ethanol (−20° C.). Centrifuge at 14,000×g for 20 min. Remove the supernatant. Wash the pellet with 800 µl of 70% ethanol (−20° C.) and centrifuge. Dry the sample, which is now partially complete double stranded target cDNA.

Example 7
Completion of the Second Strand of the Target cDNA

Resuspend the double stranded cDNA in 8 µl DEPC-treated water. Add 10 pM/2 µl Sse 8387 I adapter-oligo (dG)$_{16}$-primer. Incubate at 65° C., 10 min. Place on ice, 10 min.

3' OH End Preparation

Add reaction buffer V to a final volume of 20 µl and incubate at 37° C. for 30 min.

| Reaction buffer V |
| --- |
| 67 mM Glycine buffer (pH 9.5) |
| 10 mM 2-Mercaptoethanol |
| 6.7 mM MgCl$_2$ |
| 2 u Exonuclease I |

Add reaction buffer VI and T4 Bacteriophage DNA Polymerase 20 u to a final volume of 100 µl. Incubate at 37° C., 2 h.

| Reaction buffer VI |
| --- |
| 67 mM Tris-HCl (pH 8.8) |
| 16.6 mM (NH$_4$)$_2$SO$_4$ |
| 6.7 µM EDTA |
| 167 µg/ml BSA |
| 10 mM β-Mercaptoethanol |
| 33 µM dATP, dCTP, dGTP, dTTP |
| T4 Bacteriophage DNA Polymerase 20 u |

Extract, Precipitate

Add 100 µl of phenol:chloroform:isoamyl ethanol (25:24:1) and vortex thoroughly. Centrifuge at 14,000×g for 5 min. Transfer the upper layer to a fresh 1.5 ml microcentrifuge tube. Add 50 µl of 7.5 M NH$_4$OAc, 5 µl yeast tRNA (GIBCO BRL, Life Technologies) and 300 µl of absolute ethanol (−20° C.). Centrifuge at 14,000×g for 20 min. Remove the supernatant. Wash the pellet with 800 µl of 70% ethanol (−20° C.) and centrifuge. Dry the sample, which is now full length double stranded target cDNA with a nick.

Example 8
Second Strand cDNA Ligation

Resuspend the double stranded target cDNA pellet in 10 µl DEPC-treated water. Add reaction buffer VII to a final volume 50 µl and incubate at 22° C., 1 h.

| Reaction buffer VII |
| --- |
| 20 mM Tris-HCl (pH 7.6) |
| 5 mM MgCl$_2$ |
| 5 mM Dithiothizetol |
| 500 µg/ml Bovine Serum Albumin (Fraction 5; Sigma) |
| 0.5 mM ATP |
| Bacteriophage T$_4$ DNA Ligase 6 u |

Extract, Precipitate

Add 50 µl of phenol:chloroform:isoamyl ethanol (25:24:1) and vortex thoroughly. Centrifuge at 14,000×g for 5 min. Transfer the upper layer to a fresh 1.5 ml microcentrifuge tube. Add 12.5 µl of 7.5 M NH$_4$OAc, 5 µl yeast tRNA (Gibco BRL, Life Technologies), and 150 µl of absolute ethanol (−20° C.). Centrifuge at 14,000×g for 20 min. Remove the supernatant. Wash the pellet with 800 µl of 70% ethanol (−20° C.) and centrifuge. Dry the sample, which is now full-length double stranded cDNA.

Example 9
Coherence Termini Preparation (Not I/Sse 8387 I Digestion)

The ends of all of the double stranded cDNA and 5 µg plasmid DNA vector (pSPORT 1) are then prepared for ligation. Not I digestion is accomplished first. The cDNA and the plasmid reactions are performed in different tubes. For each reaction, 10 to 20 u of enzyme is used.

| Not I Reaction buffer |
| --- |
| 6 mM Tris-HCl (pH 7.9) |
| 6 mM MgCl$_2$ |
| 150 mM NaCl |
| 1 mM DTT |
| 0.5 u Not I/µl reaction buffer |

Incubate at 37° C., 3 h (final volume 20 µl).

Then the other cDNA ends and the plasmid are prepared with the other enzyme.

| Sse 8387 I Reaction buffer |
| --- |
| 10 mM Tris-HCl (pH 7.5) |
| 80 mM KCl |
| 7 mM β-Mercaptoethanol |
| 0.5 u Sse 8387 I/µl reaction buffer |

Incubate at 37° C., 3 h (final volume 50 µl).

Extract, Precipitate

Add 50 µl of phenol:chloroform:isoamyl ethanol (25:24:1) and vortex thoroughly. Centrifuge at 14,000×g for 5 min. Transfer the upper layer to a fresh 1.5 ml microcentrifuge tube. Add 12.5 µl of 7.5 M NH$_4$OAc, 5 µl yeast tRNA (GIBCO BRL, Life Technologies), and 150 µl of absolute ethanol (−20° C.). Centrifuge at 14,000×g for 20 min. Remove the supernatant.

Wash the pellet with 800 µl of 70% ethanol (−20° C.) and centrifuge. Dry the samples, one tube having cDNA with cohesive termini and one tube having vector with cohesive termini.

Example 10
Ligation of All of the cDNA to the Plasmid Vector (pSPORT 1)

| Reaction buffer VIII |
| --- |
| 50 mM Tris-HCl (pH 7.6) |
| 5 mM MgCl$_2$ |
| 0.5 mM ATP |
| 5 mM DTT |
| 500 µg/ml Bovine Serum Albumin (Fraction 5; Sigma) |
| 2.5 µg/ml plasmid pSPORT 1, Not I/Sse 8387 I-cut cDNA |
| 25 u/ml T4 DNA Ligase |

Incubate at 4° C., overnight.

| Example of a 20 µl reaction: |
| --- |
| 11.5 µl water |
| 2 µl 10X Reaction Buffer VIII |
| 5 µl (all) cDNA |
| 0.5 µg/2 µl vector |
| 1 µl T4 Ligase |

Example 11
E. coli Ligated cDNA Transformation by Electroporation

Combine 20 µl ligation reaction (standard recipes may be found in protocol manuals) 5 µl yeast tRNA, 12.5 µl 7.5 M NH$_4$OAc, and 75 µl 100% ethanol (−20° C.). Vortex the mixture. Centrifuge at 14,000×g, 20 min, at room temperature. Wash the pellet with 800 µl of 70% ethanol (−20° C.). Centrifuge at 14,000×g, 5 min, at room temperature, twice. Dry the ligated sample.

Add 3 µl of sterile, distilled water to the dried pellet. Add 1 µl of the ligated cDNA/pSPORT 1 to 50 µl of electrotransformable cells such as ELECTROMAX DH10B™ cells, and electroporate. Other methods of transformation may be used, but electroporation is preferred because it is the most efficient. Efficient transformation of ELECTROMAX DH10B™ Cells requires a field strength of ≠16.6 kV/cm and a pulse length of 4 to 5 ms [Life Technologies, ELECTROMAX DH10B™ Cells, Cat. No.: 18290–015]. Add 1 ml of S.O.C. medium [described in the Life Technologies product sheet] to the electroporated cells and incubate them at 37° C. for 1 h with vigorous aeration.

Plate the cells on LB plates containing 100 µg/ml Ampicilin, incubate the plates overnight at 37° C.

Example 12
Sequence Confirmation of Full Length Target Molecule

1. Plasmid Purification by using Wizard Lambda Preps: DNA Purification System [Cat. No.: A7290. Promega]

Culture a single bacteria clone that contains a constructed plasmid in 5 ml LB plus Ampicilin (100 ug/ml) at 37° C. for 16–18 h with vigorous aeration. Centrifuge the cultures at 4000×g for 5 min. Dissolve the bacteria pellet in 500 µl of Cell Resuspension Buffer (50 mM Tris-HCl (pH7.5); 10 mM EDTA; 100 µg/ml RNase A). Add 500 µl of Cell Lysing Solution. Keep at room temperature for 5 min (0.2 M NaOH and 1% SDS). Add 500 µl of Neutralization Solution. Keep on ice for 15 min (1.32 M Potassium Acetate). Centrifuge the sample at 14,000×g for 15 min. Mix the supernatant with 800 µl of Resine Buffer. Recipes for the three previously mentioned solutions and buffers can be found in Promega materials and in the Book of Molecular Cloning (as Solutions I, II, and III). Keep at room temperature for 5 min.

Load the mixture on the column. Wash the column with 3 ml of Column Washing Buffer (80 mM Potassium acetate; 8.3 mM Tris-HCl (pH 7.5); 40 µM EDTA; 55% ethanol). Dry the column by centrifugation at 14,000×g for 1 min. Elute the plasmid DNA with 50 µl distilled water by the centrifugation. Check the concentration with standard methods, such as a spectrophotometer.

2. Sequencing Analysis of Both Ends of Full Length Target cDNA

A preferred sequencing tool is the Perkin-Elmer Applied Biosystems 377 Prism DNA Sequencer. In fluorescent sequencing, the extended and terminated DNA molecules are labeled with fluorescent dyes, rather than with radioactivity. Reactions are electrophoresed through modified acrylamide gels using quartz plates. As the molecules pass through a region near the bottom of the gel (36 cm from the well), a laser passes over the gel, exciting the dyes and detecting their emissions. The data is interpreted by the computer and the base sequence is determined. The data received is in the form of an electropherogram. The primers are T7 (5' TA ATA CGA CTC ACT ATA GGG 3', SEQ ID NO:3), and SP6 (5' GAT TTA GGT GAC ACT ATA G 3', SEQ ID NO:4). All references cited in this patent application are herein incorporated by reference to the same extent as though each individual reference had been incorporated.

What is claimed is:

1. A method for constructing full-length target cDNA sequences, comprising the steps:
   a) isolating mRNA and synthesizing first strand cDNA sequences from the mRNA;
   b) degenerating the mRNA;
   c) hybridizing forward primers to the first strand cDNA sequences, the forward primers being complementary to the target cDNA sequences wherein only first strand cDNA sequences that are target cDNA sequences hybridize with the forward primers;
   d) synthesizing second strand cDNA sequences around the forward primers to form full-length double-stranded target cDNA sequences;
   e) isolating the full-length double-stranded target cDNA sequences, the full-length double-stranded target cDNA sequences having two ends; and
   f) modifying both ends of the full-length double-stranded target cDNA sequences wherein the 3' ends are distinct from and incompatible with the 5' ends.

2. A method for constructing full-length target cDNA sequences, comprising the steps:
   a) isolating mRNA having 3' poly(A) tails;
   b) annealing first adapter-primers to the 3' poly(A) tails of the mRNA, the first adapter-primers comprising a first enzyme recognition sequence on the 5' ends and poly(dT) on the 3' ends;
   c) synthesizing first strand cDNA sequences from the first adapter-primers annealed to the mRNA;
   d) degenerating the mRNA;
   e) adding poly(dC) nucleic acid tails to the 3' end of the first strand cDNA sequences;
   f) hybridizing forward primers to the first strand cDNA sequences, the forward primers being complementary to the target cDNA sequences, wherein only first strand cDNA sequences that are target cDNA sequences hybridize with the forward primers;
   g) synthesizing 3' portions of second strand cDNA sequences from the forward primers to form partially double-stranded target cDNA sequences;
   h) isolating the partially double-stranded target cDNA sequences;
   i) hybridizing second adapter-primers to the poly(dC) nucleic acid tails of the 3' end of the first strand cDNA sequences, wherein the second adapter-primers comprise a second enzyme recognition sequence on the 5' ends and poly(dG) on the 3' ends; and
   j) synthesizing 5' portions of the second strand cDNA sequences between the second adapter-primers and the forward primers, thereby creating full-length double-stranded target cDNA sequences.

3. The method according to claim 2 wherein the first strand cDNA sequences are synthesized with Moloney Murine Leukemia Virus Reverse Transcriptase.

4. The method according to claim 2 wherein the second strand cDNA sequences are synthesized with a DNA dependent DNA polymerase.

5. The method according to claim 2 wherein the partially double-stranded target cDNA sequences are isolated from the single-stranded cDNA sequences by an affinity column of oligo(dA) cellulose.

6. The method according to claim 5 wherein a 5'-exonuclease is used in a last elution of the affinity column for degrading residual single stranded cDNA.

7. The method according to claim 6 wherein the 5'-exonuclease is mung bean nuclease.

8. The method according to claim 2 wherein the 5' portions of the second strand cDNA sequences are synthesized with $T_4$ DNA polymerase.

9. The method according to claim 2 wherein a nick is left unfilled between the synthesized 5' portions of the second strand cDNA sequences of step j and the forward primers, and wherein the nick is sealed with $T_4$ ligase.

10. The method of claim 2 further comprising the step:

cutting the full-length double-stranded target cDNA sequences with a first enzyme at the first enzyme recognition sequence and a second enzyme at the second enzyme recognition sequence.

11. The method of claim 10 further comprising the step:

cutting a vector with the first enzyme and the second enzyme and ligating the cut full-length double-stranded target cDNA sequences into the cut vector.

12. The method according to claim 11 wherein the vector has multiple cloning sites for enzymes, polymerase promoters and a marker.

13. The method according to claim 2 wherein the forward primers anneal near the 3' end of the first strand cDNA sequences.

14. The method according to claim 2 wherein the length of the forward primers are between 10 and 50 nucleotides.

15. The method according to claim 14 wherein the length of the forward primers are between 22 and 35 nucleotides.

16. The method of claim 11 further comprising the steps:

introducing the ligated vector containing the full-length double-stranded target cDNA sequences into host cells;

multiplying the host cells; and isolating the full-length double-stranded target cDNA sequences from the host cells.

17. The method according to claim 2 wherein the poly (dC) nucleic acid tails are added with terminal deoxynucleotidyl transferase.

* * * * *